United States Patent
Brucker (10) Patent No.: US 6,296,657 B1
(45) Date of Patent: *Oct. 2, 2001

(54) VASCULAR SEALING DEVICE AND METHOD

(76) Inventor: Gregory G. Brucker, 5029 Garfield Ave. S., Minneapolis, MN (US) 55419-1252

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/167,876

(22) Filed: Oct. 7, 1998

(51) Int. Cl.[7] ................................................ A61B 17/03
(52) U.S. Cl. ........................................ 606/213; 606/192
(58) Field of Search ..................... 606/158, 191–193, 606/213–214, 61

(56) References Cited

U.S. PATENT DOCUMENTS

| | | | |
|---|---|---|---|
| 4,467,806 | * | 8/1984 | Bhiwandiwala et al. .......... 606/193 |
| 4,878,495 | * | 11/1989 | Grayzel ................................. 606/193 |
| 4,890,612 | * | 1/1990 | Kensey ................................. 606/213 |
| 5,383,889 | * | 1/1995 | Warner et al. ...................... 606/192 |
| 5,413,571 | * | 5/1995 | Katsaros et al. ................... 606/213 |
| 5,443,495 | * | 8/1995 | Buscemi et al. ................... 606/191 |
| 5,545,176 | * | 8/1996 | Murtfeldt ............................ 606/192 |
| 5,624,399 | * | 4/1997 | Ackerman ........................... 606/193 |
| 5,653,730 | * | 8/1997 | Hammerslag ....................... 606/214 |
| 5,669,909 | * | 9/1997 | Zdeblick et al. ................... 606/61 |
| 5,728,134 | | 3/1998 | Barak . |
| 5,830,130 | | 11/1998 | Janzen . |

* cited by examiner

Primary Examiner—David O. Reip
(74) Attorney, Agent, or Firm—Beck & Tysver, P.L.L.C.

(57) ABSTRACT

A vascular closure device. In each embodiment, the device includes at least one relatively non-deformable surface member and a conformable and distensible member. Typically the conformable member is implemented as a balloon structure that is inflated with a liquid or gaseous medium. This inflation fluid increases the fluid pressure in the balloon which counteracts the fluid pressure of the punctured vessel. The resulting forces on the balloon are opposed by tissue structures that transfer the load to the surrounding subcutaneous tissue structures. The device may be constructed of bioabsorbable or non-bioabsorbable materials. Additionally, the device may be coated with agents to provide a secondary therapy for enhancement of clotting or prevention of infections. These agents may also elute from the distensible conformal member.

15 Claims, 8 Drawing Sheets

VASCULAR SEALING DEVICE AND METHOD

FIELD OF THE INVENTION

The present invention relates generally to vascular catheterization and more particularly to vascular closure devices which are used to stem bleeding from surgical procedures that penetrate blood vessels.

BACKGROUND OF THE INVENTION

Minimally invasive surgical techniques have become the method of choice for the treatment of certain cardiovascular diseases. During interventional cardiology procedures, small plastic tubes called catheters are inserted into the vasculature through a leg or an arm. These catheters are threaded to the appropriate location for the diagnostic or therapeutic procedure. The access or opening in the artery or vein is created by using the so-called Seldinger technique. The Seldinger procedure begins with the insertion of a hollow needle through the skin to puncture the desired blood vessel. Next a guidewire is inserted through the needle into the blood vessel. At this point the needle is withdrawn and the guidewire remains in place. An introducer sheath or cannula is placed over the guidewire and inserted into the vessel to dilate or stretch the vessel to the required diameter for catheter insertion. The introducer also seals against blood pressure, thus preventing bleeding from the puncture site while allowing access to the cannulated vessel. The introducer remains in place until the procedure is completed. After the procedure, the introducer is removed leaving a wound in the skin and an opening in the blood vessel. This injury is subject to significant bleeding because the patient usually receives blood thinners or anticoagulants to minimize or prevent clot formation during the intervention. While these medications make the procedure safer, they also make sealing the puncture site upon removal of the introducer more difficult. The effect of blood thinners is to reduce the clotting capacity of the blood meaning that it will take longer for cuts and injuries to heal. Historically, after removal of the introducer, manual pressure has been applied for up to several hours to the puncture site and subsequently the canulated extremity is immobilized for up to a full day until sufficient healing has occurred.

Using manual pressure increases hospital staff time, increases health care costs, is uncomfortable for the patient, and increases the time to ambulation. Vascular sealing devices have been developed to address these issues. U.S. Pat. Nos. 4,744,364; 4,852,560, and 4,890,612 describe a mechanical umbrella which is inserted into the opening of the vessel and seals against blood flow from the inside of the vessel. U.S. Pat. Nos. 5,391,183 and 5,437,631 describe a plug which mechanically fills tie hole in the extremity with a material while allowing natural healing of the vessel to occur. U.S. Pat. No. 5,413,571 teaches a device which enters the vessel to be sealed. Both of these methods have the added risk of potentially injecting foreign materials into the blood vessel which may cause added complications. U.S. Pat. No. 5,613,974 describes a method to mechanically seal the puncture site in the artery or vein with sutures much like closing an incision in the skin. These methods typically require a skilled person, require significant time and are relatively expensive. U.S. Pat. Nos. 5,728,132 and 5,626,601 describe the use of hemostatic agents such as fibrin activated blood to provide a mechanical seal at the wound site. The patients' blood is typically drawn prior to the procedure and activated before injection into the puncture site. For various reasons each of the above described methods have not been fully accepted by the medical community. Consequently, there is a continuing need to develop devices which address wound closure to reduce times and health care costs.

SUMMARY

Several embodiments of the inventive vascular closure device are shown. In each embodiment, the device includes at least one relatively non-deformable surface member and a conformable and distensible member or portion. Typically the conformable member is implemented as a balloon structure that is inflated with a liquid or gaseous medium. This inflation fluid increases the fluid pressure in the balloon which counteracts the fluid pressure of the punctured vessel. The resulting forces on the balloon are opposed by tissue structures that transfer the load to the surrounding subcutaneous tissue structures. Additional structures may be added to the device to supplement these functions as typified by an adhesive patch or ribs.

Additionally, the balloon functions to supply a flexible external cover over the opening in the vessel with sufficient force to maintain the cover against the opening in the vessel. This seals the subcutaneous hole caused by the puncture and prevents loss of blood, all of which allows natural healing to occur in the opening created in the vessel. After the wound is healed, the sealing device may be removed by grasping the non-deformable portion and withdrawing the device. At this time normal wound care management treatments are applied.

In an alternate embodiment the device may remain in place and degrade biologically.

In addition, the device may be coated with agents to provide a secondary therapy such as drugs for enhancement of clotting or prevention of infections. These agents may also elute from the distensible conformal member.

The use of this device permits the cutaneous structures to heal more quickly without excessive bleeding and also allows for the patient to ambulate more quickly.

BRIEF DESCRIPTION OF THE DRAWINGS

The several illustrative embodiments of the device shown in the figures share structural elements and like reference numerals are used to identify identical structure throughout the views, wherein.

DETAILED DESCRIPTION

Figure 1A:
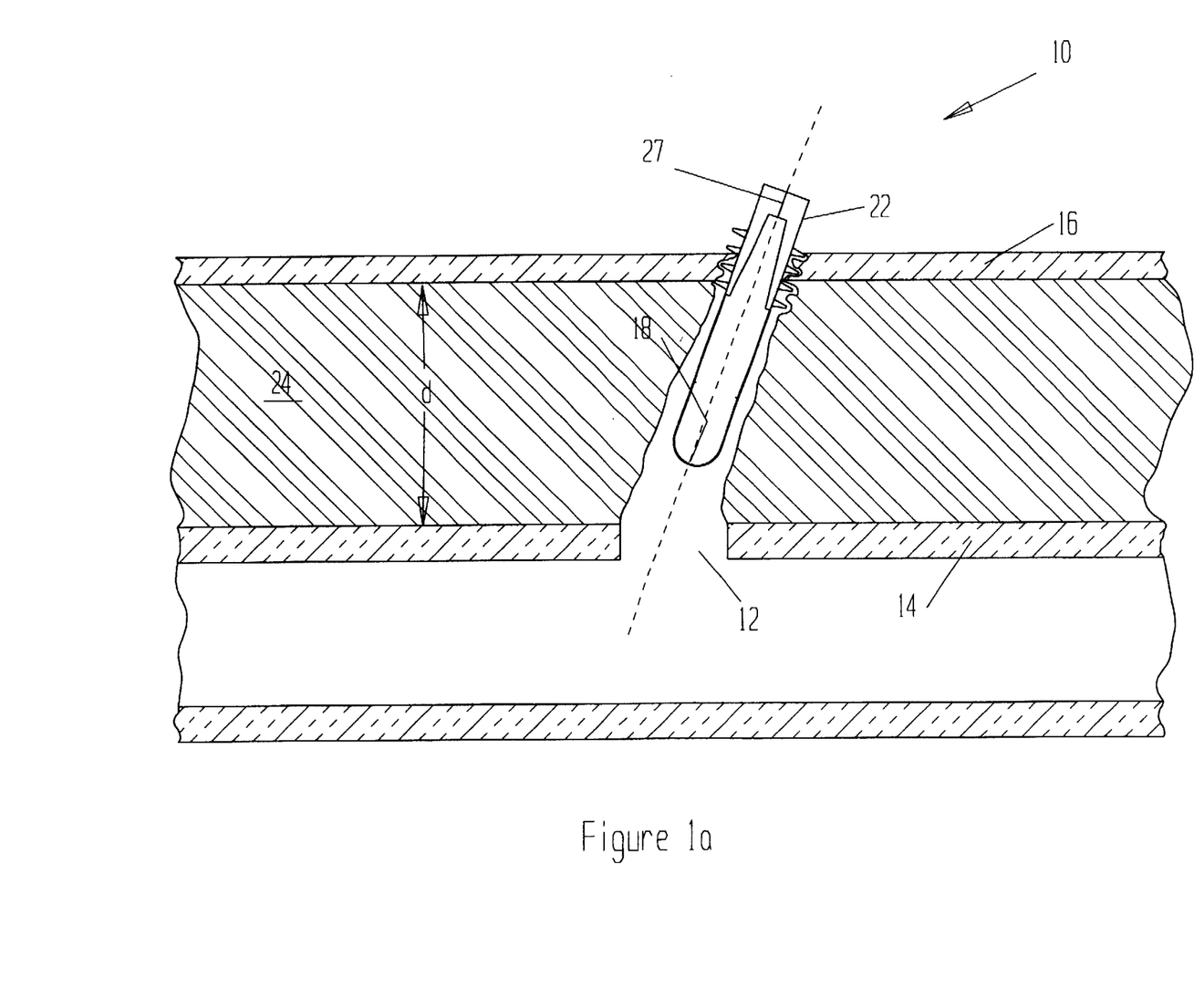
FIG. 1a shows a first embodiment device placed near a vessel.

FIG. 1a is a schematic drawing that shows a first embodiment of the device 10 inserted into a surgical wound 12 in the patient 16. In the figure, the surgical wound 12 was used to provide access to the vessel 14 located subcutaneously in tissues 24, a distance "d" away from the surface of the skin. In the figure, the device 10 has been inserted into the wound 12 after the cannula or vascular introducer has been removed.

The device 10 can be conceptually divided into at least two sections or portions to facilitate a discussion of the structure and operation of the device 10. The distal tip of the device 10 is formed as a distensible conformable member 18 or portion. The conformable member 18 is connected to a second portion called the surface member 22. After insertion into the wound 12 area the device is activated and "filled" through a septum 27. The "filled" state is shown in FIG. 1b.

Figure 1B:
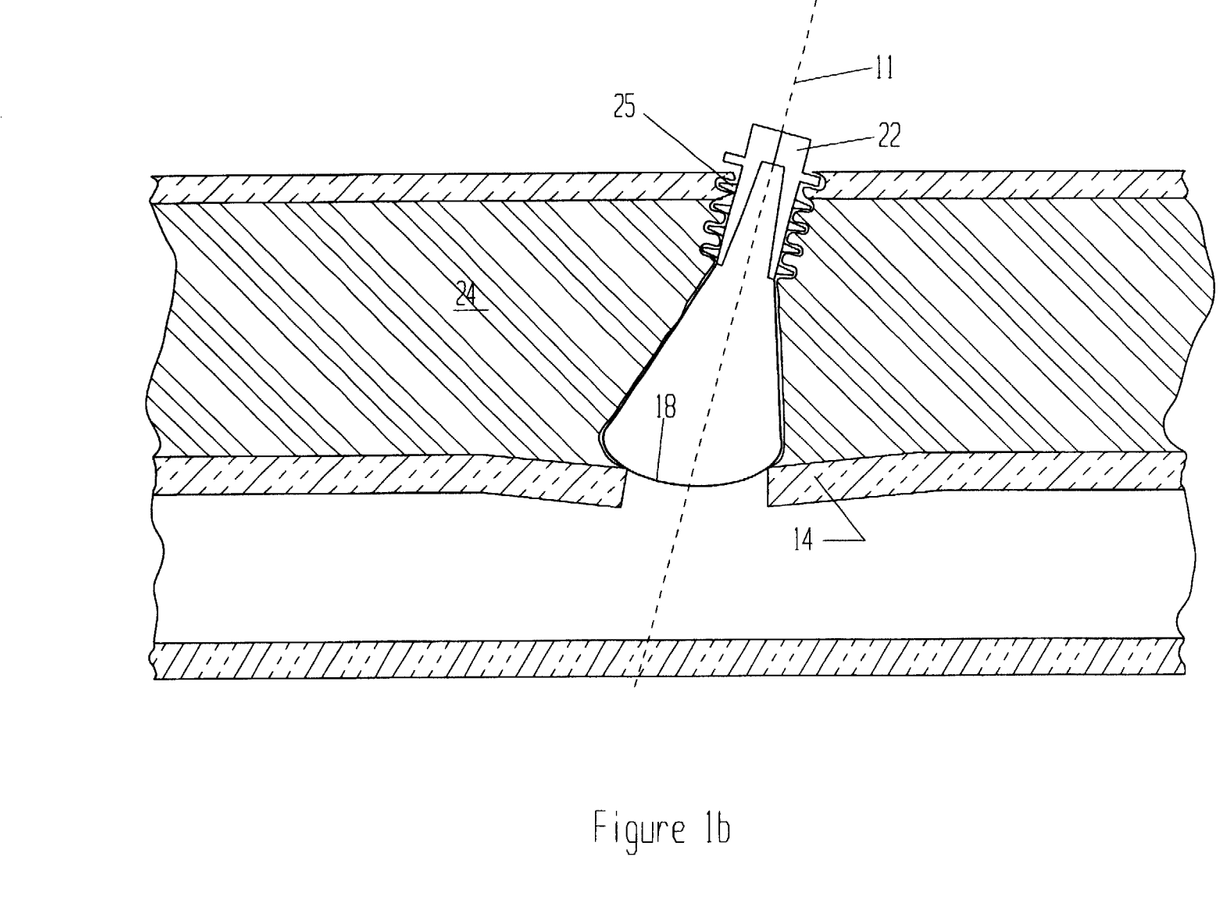
FIG. 1b shows a first embodiment device inflated to seal a vessel.

As seen in FIG. 1b, the distensible member 18 expands from the unactivated shape shown in FIG. 1a to the distended shape seen in the figure and thus interacts with the soft tissue 24 of the wound 12 to support and to position the conformable distensible member 18 near the vessel 14. In this embodiment the distensible member 18 lengthens in an axial direction along the axis 11 as a fluid (gas or liquid) is introduced through the septum 27(FIG. 1a ). In this embodiment, ribs typified by rib 25, located near the surface member 22 may provide an opposing force or "traction" to the expanded distal conformable distensible member 18. The surface member 22 may also provide skin closure and also provide a seal against the leakage of blood. The surface member 22 also provides a convenient location to grasp the device 10 for removal after the vessel 14 has closed. The septum 27 may be used to deflate the distensible section 18 to facilitate removal.

In general the conformable and distensible member 18 at the distal tip expands to cover the incision in the vessel 14 with a flexible, membrane structure creating a sealing structure which, in conjunction with the surrounding tissue 24, effectively seals the blood vessel 14 and displaces blood from the wound area thus preventing bleeding from the skin of the patient 16. Although it is difficult to quantify the forces involved both surface member 22 and distensible member 18 carry the complimentary forces which resist the pressure of the blood vessel 14 communicated through the distal conformable member 18. It is likely that three separate sealing mechanisms are at work in the device 10. In one instance the device 10 closes off the vessel 14 in a manner analogous to direct pressure on the wound. In another aspect, blood "leaking" from the vessel is contained within the wound 12 and the device 10 prevents this blood from "leaking" out of the wound by closing off the skin which equalizes the pressure in the wound with the pressure in the vessel 14. In another aspect, the device forms a seal over the opening in the vessel preventing leaking from the vessel into the wound but allowing flow to continue through the vessel. In all instances, pressure in the device opposes the blood pressure in the vasculature. Once the vessel 14 stops bleeding the device 10 is removed allowing for the use of a conventional bandage and wound care treatments. In the intervening time, the patient may be ambulatory as the device will conform to anatomical changes caused by motion of the extremity.

Figure 2:
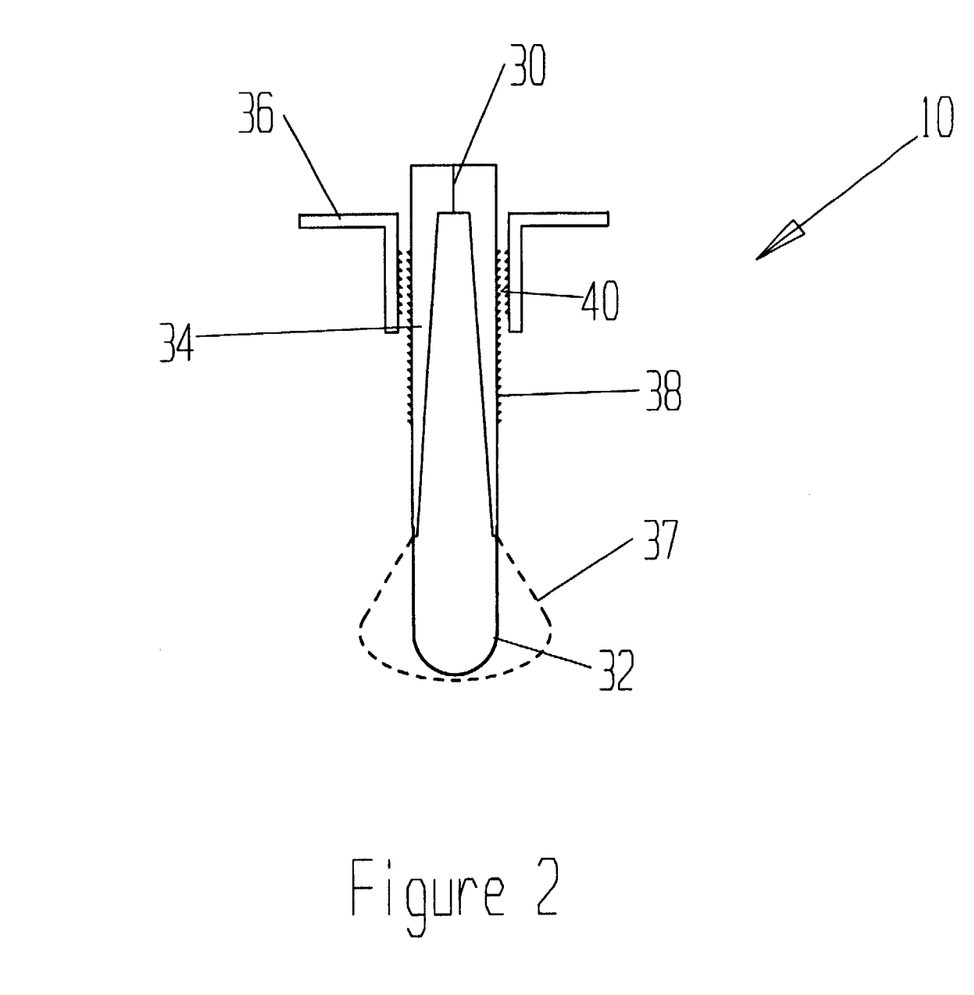
FIG. 2 shows a second embodiment of the device.

FIG. 2 shows a specific implementation of a second embodiment of the device 10 where three functional features are implemented as a two piece construction with four distinct physical elements. The pieces are a ring or collar 36 and an adjustable stem 34. These two pieces can be moved with respect to each other. The stem 34 is adjustable within the collar 36. In the figure annular locking ribs typified by rib 38 interacts with a complimentary rib 40 on the collar 36 structure to permit adjustment. A conventional screw thread may be used instead of the ribbed structure.

This version of the device 10 includes a distinct stem 34 which includes a septum valve 30, which communicates to the interior of a balloon 32. The balloon inflates to form the distal conformable distensible member. The balloon merges into the stem section 34 which has a variable thickness wall. In use, the physician can size the device length ("d" in FIG. 1a) to a particular patient by positioning the stem 34 within the collar 36 then inserting the device into the wound. In operation, balloon member 32 expands to provide the covering and seal of the opening in the blood vessel. Once again the inflation fluid may be either a viscous liquid or a gas. When lightly inflated in free space the balloon member distends into the shape indicated by the dotted line 37. It should be clear that the distal distensible member may have other expanded shapes within the scope of the disclosure.

Figure 3:
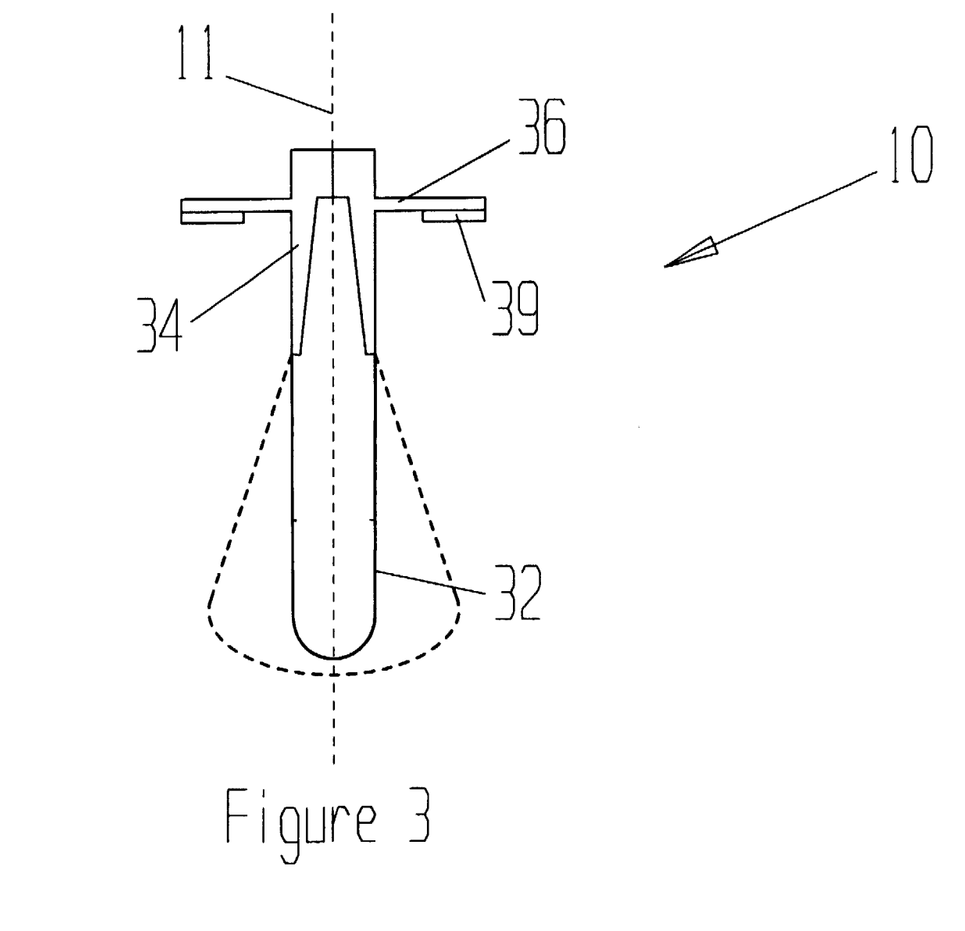
FIG. 3 shows a third embodiment of the device.

FIG. 3 shows a third specific implementation of the device 10 formed as a unitary structure. In this embodiment a very flexible and distensible balloon member 32 accommodates the depth "d" of the vessel. In general the device 10 may grow in length along axis 11 and grow in girth in a non-uniform way along the axis 11. In contrast to the FIG. 2 design, the balloon is both longer and has a fixed thickness thin wall over most of its extent. The stem portion 34 is relatively shorter, stiffer and integrated with the surface contacting collar 36. An adhesive layer 39 may be provided on the surface collar 36 to adhere the collar to the skin of the patient. In this design the stiffness of the stem is determined primarily by the need to push the device 10 into the wound. In operation the balloon 32 is inflated and conforms to the vessel. The sides of the balloon also engage the tissue near the vessel and provide a seal against the tissue surfaces.

Figure 4:
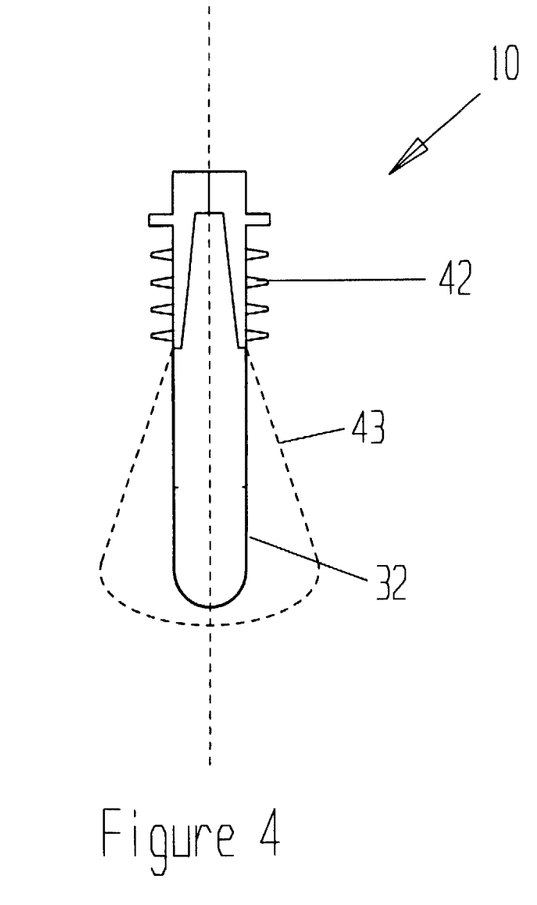
FIG. 4 shows a first embodiment of the device.

FIG. 4 shows a specific embodiment of the device identical to the one illustrated in FIG. 1a and FIG. 1b. In this view the unconstrained shape under inflation is shown in dotted outline 43. In this version of the device, unitary ribs, illustrated by rib 42 on the stem interact with the tissue structure near the vessel. In this embodiment the balloon 32 expands the ribs into contact with the tissue structure thus holding the device in the wound and providing the requisite complimentary force to resist the expansion of the distal conformable balloon member 32. In contrast to other embodiments this version should be less influenced by inflation pressure.

Figure 5:
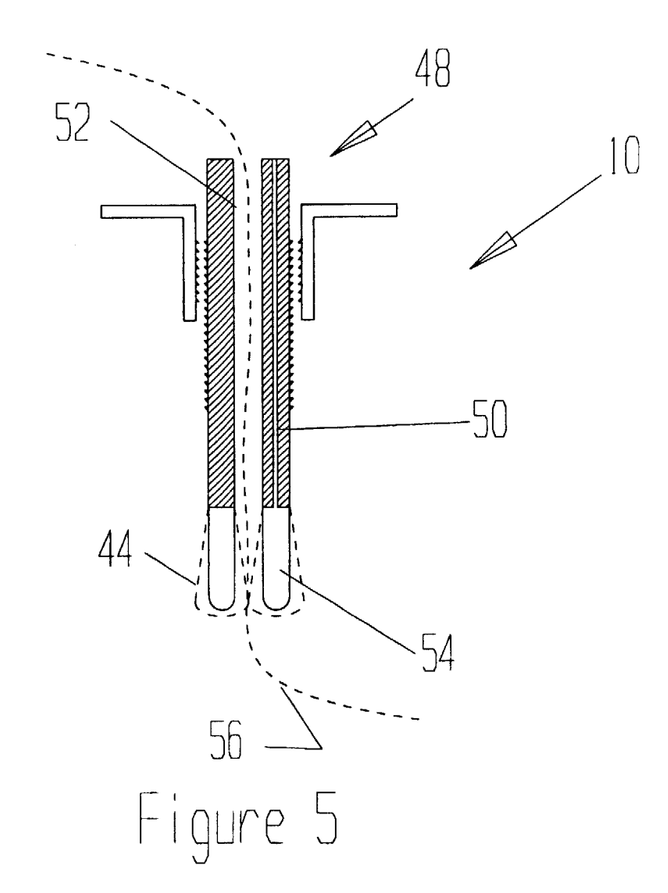
FIG. 5 shows a fourth embodiment of the device.

FIG. 5 shows an alternate fourth embodiment of the device 10, which includes a septum/inflation lumen 50 connecting the surface portion 48 to a donut shaped distal balloon 54. In this version of the device, a through lumen 52 is provided so as to maintain access to the vessel. In use, the physician may withdraw the bulky catheter devices and yet retain an interventional device 56, typically a guidewire, in the vessel for later use. The lumen 52 provides access to the vessel site for other interventions or therapies. In this embodiment the balloon 54 seals against the vessel and the interventional device 56 as indicated by the dotted line 44. It should be appreciated that the donut balloon structure can be used with either the adjustable length structures shown as well as the fixed length embodiments.

Figure 6:
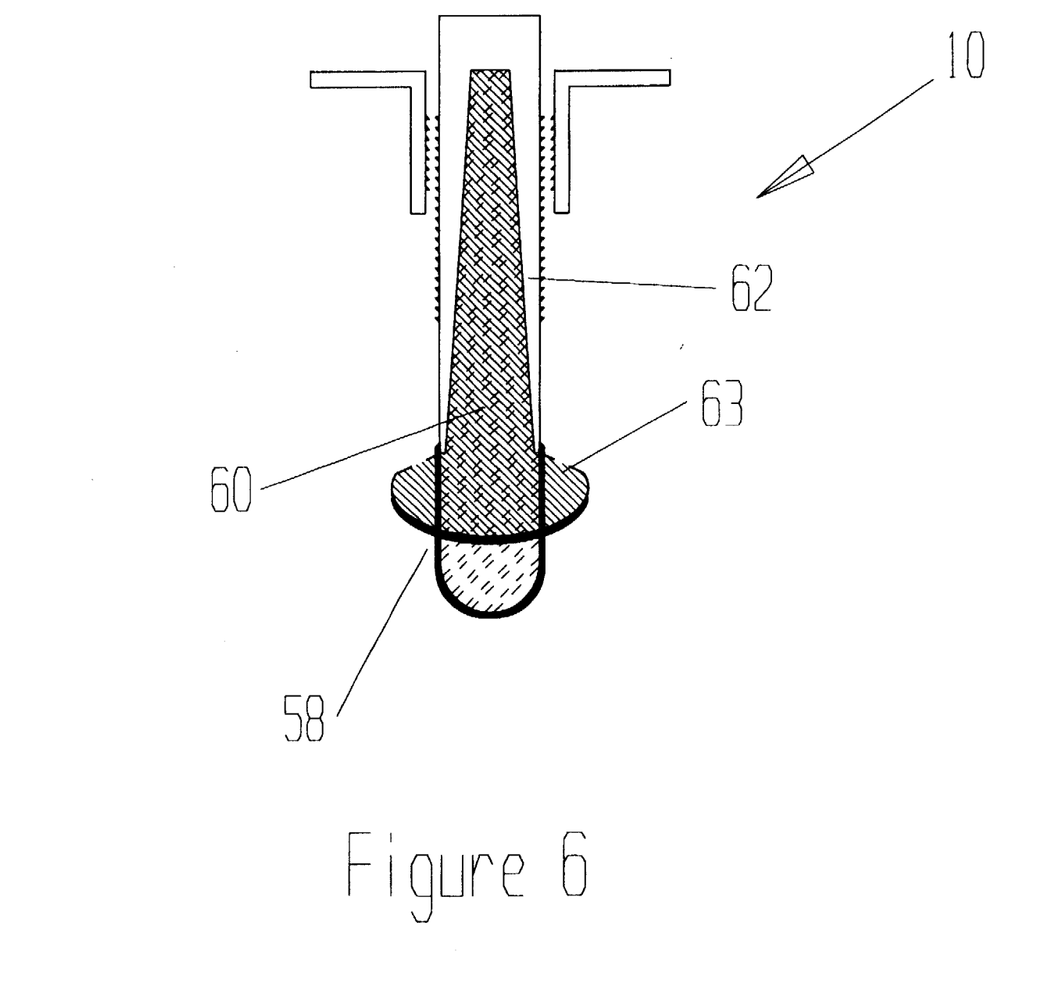
FIG. 6 shows a fifth embodiment of the device.

FIG. 6 shows another version of the device 10 where the gentle force functionality is carried out by a deformable gel material 60. In this version the stem portion 62 includes a material which is soft enough to conform to the shape of the vessel and provide a contiguous seal at the site of the incision. This material may also be shaped to the anatomical structures of the soft tissue to form an effective seal and provide the required complimentary forces. It is preferred in this embodiment to have a balloon membrane 63 to isolate the gel from the blood although this membrane may be permeable so as to elute a secondary therapy such as a clotting agent or antibacterial medication. The surface shading 58 on the distend dotted outline of the balloon is intended to indicate a bactericide or other drug or coating. In this particular drawing the device has no increase in volume but rearranges the interior material 60 to form the conformable distensible member 63. It should be noted that the drug material could elute or emerge from the interior of the device 10 through a porous membrane forming the distensible member 63.

Figure 7:
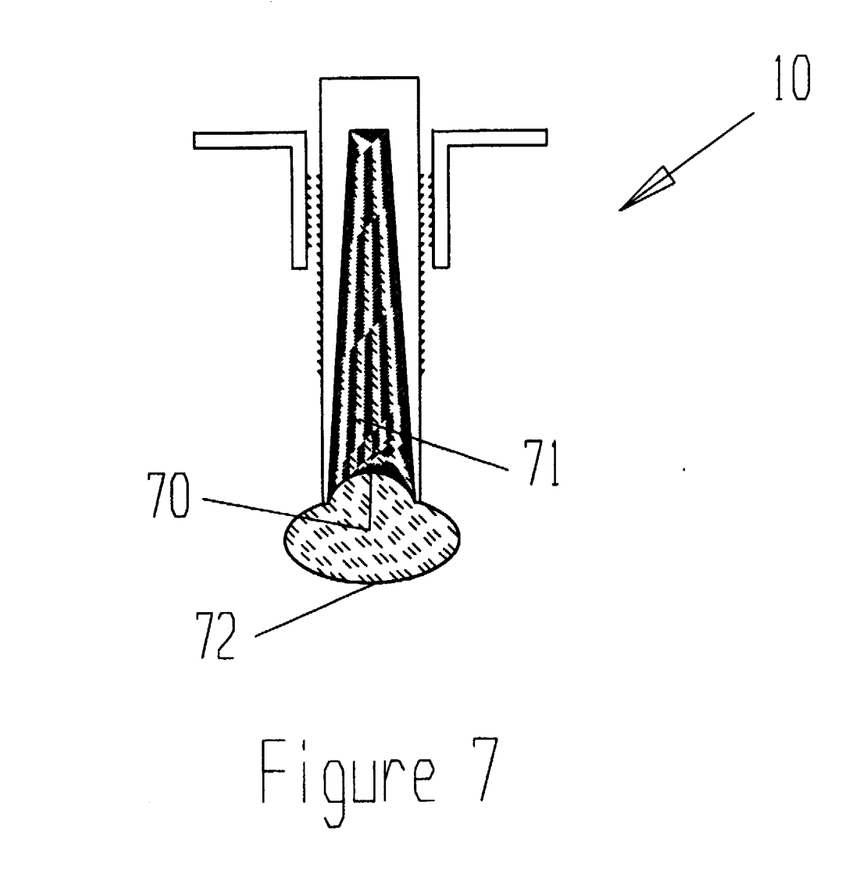
FIG. 7 shows a sixth embodiment of the device.

FIG. 7 shows an alternate embodiment of the device which includes an expandable foam core member 71 which increases in volume in the presence of blood i.e. swells in the presence of blood or simply remains flowable when the device is placed in the wound. In this device the swelling is localized to the vessel interaction area. The concave surface 70 shows the device in the inserted and inactivated state, while the solid outline 72 shows the localized swelling mode. The outer periphery of the structure shown in the figure represents the device with both shape change and volume increase. Any of a variety of materials have the propensity to increase in volume when exposed to blood including hydrogels and hydrophylic materials.

Each of the various embodiments of the device may be enhanced by the inclusion of particular coatings. It is believed that antimicrobial coatings will reduce clinical issues presented by the insertion of a device after surgery. Although numerous organic and non-organic coatings may be used it is expected that photoactivated materials such as that supplied by SurModics, formerly BSI, will be especially suitable.

In all of the embodiments, the device may be constructed from conventional thermoplastic or thermoelastic plastics such as "Pellathane" and silicones. It may also be desirable to form all or part of the device from a biodegradable thermoplastic material such as polyglatide. Depending on composition among other variables such a device will degrade in the body within a short period of time not more than several weeks.

What is claimed is:

1. A device for sealing a vascular access wound in a patient, which includes both a skin puncture and a vessel punctured for vascular access, said device comprising:
   a) a surface member for placement proximate the patient's skin at the location of said wound, said skin defining a substantially horizontal plane;
   b) a conformable distensible member having an approximately vertical axis which is approximately perpendicular to said horizontal plane, said conformal distensible member for location proximate said vessel, and coupled to said surface member;

said conformable distensible member capable of shape change upon expansion whereby said device seals said vessel by extending the length of said conformal distensible member in the direction along said approximately vertical axis.

2. The device of claim 1 wherein said conformable distensible member can change both shape and volume while increasing in length along said approximately vertical axis.

3. The device of claim 2 wherein said conformable distensible member is a balloon.

4. The device of claim 1 wherein said conformable distensible member is inflated with a gas to cause expansion.

5. The device of claim 4 wherein said conformable distensible member is coupled to a septum, whereby said distensible member may be inflated with a fluid introduced through said septum.

6. The device of claim 1 wherein said conformable distensible member is inflated with a liquid to cause expansion.

7. The device of claim 1 wherein said surface member includes a flange having a compliant adhesive patch for temporary contact with said skin.

8. The device of claim 1 wherein said surface member includes a plurality of ribs for temporary contact with said skin.

9. The device of claim 1 wherein said surface member and said conformable distensible member are made from a non-biodegradable material.

10. The device of claim 1 wherein said conformal distensible member can increase in volume after insertion into said wound by absorption of fluid from said wound to cause expansion of the conformal and distensible member toward said vessel along said approximately vertical axis.

11. The device of claim 1 wherein said conformable distensible member can change in shape but not volume after insertion into said wound.

12. The device of claim 1 wherein said conformable distensible member has a lumen therein allowing access to the vessel while the device is in place in said wound.

13. A device for sealing a vascular access wound in a patient, which includes both a skin puncture and a vessel punctured for vascular access, said device comprising:
   a) a surface member for placement proximate the patient's skin at the location of said wound;
   b) a conformable distensible member proximate said vessel, coupled to said surface member, said conformable member capable of shape change but not volume change, whereby said device seals said vessel in part by extending the length of said distensible member in a direction along an approximately vertical axis.

14. A device for sealing a vascular access wound in a patient, which includes both a skin puncture and a vessel punctured for vascular access, said device comprising:
   c) a surface member for placement proximate the patient's skin at the location of said wound, said surface member includes a plurality of ribs for temporary contact with said skin, said skin defining a substantially horizontal plane;
   d) a conformable distensible member having an approximately vertical axis which is approximately perpendicular to said horizontal plane, said conformal distensible member for location proximate said vessel, and coupled to said surface member;

said conformable distensible member capable of shape change upon expansion whereby said device seals said vessel by extending the length of said conformal distensible member in the direction along said approximately vertical axis.

15. A device for sealing a vascular access wound in a patient, which includes both a skin puncture and a vessel punctured for vascular access, said device comprising:
   e) a surface member for placement proximate the patient's skin at the location of said wound, said skin defining a substantially horizontal plane;
   f) a conformable distensible member having an approximately vertical axis which is approximately perpendicular to said horizontal plane, said conformal distensible member for location proximate said vessel, and coupled to said surface member, said conformable distensible member having a lumen therein allowing access to the vessel while the device is in place in said wound;

said conformable distensible member capable of shape change upon expansion whereby said device seals said vessel by extending the length of said conformal distensible member in the direction along said approximately vertical axis.

* * * * *